United States Patent [19]

Duyfjes

[11] 4,160,029

[45] Jul. 3, 1979

[54] PROCESS FOR THE PREPARATION OF A WATER-SOLUBLE COMPLEX OF 2-(4'-THIAZOLYL)BENZIMIDAZOLE AND FOR THE PREPARATION OF ANTHELMINTIC FUNGICIDAL COMPOSITIONS

[75] Inventor: Werner Duyfjes, Bloemendaal, Netherlands

[73] Assignee: Merck & Co., Inc., Rahway, N.J.

[21] Appl. No.: 794,505

[22] Filed: May 6, 1977

[30] Foreign Application Priority Data

May 10, 1976 [NL] Netherlands ......................... 7604976

[51] Int. Cl.² ........................................... C07D 277/20
[52] U.S. Cl. .................................... 424/258; 424/270; 260/302 H; 546/168; 546/179

[58] Field of Search ........................ 260/302 H, 286 R; 424/258, 270

[56] References Cited

U.S. PATENT DOCUMENTS

| 3,475,444 | 10/1969 | La Pierre | 260/302 H |
| 3,535,331 | 10/1970 | Glamkowski | 260/302 |
| 3,538,108 | 11/1970 | Pines | 260/302 H |
| 3,658,827 | 4/1972 | Bezou | 260/302 H |

Primary Examiner—Nicholas S. Rizzo
Attorney, Agent, or Firm—David L. Rose

[57] ABSTRACT

Highly soluble complexes of 2-(4'-thiazolyl)benzimidazole are prepared using glycolic acid. The aqueous solutions prepared therefrom are stable and may be used for anthelmintic and antifungal purposes. Additional compounds, especially other fungicidal agents, may be combined for compositions of broad spectrum.

7 Claims, No Drawings

PROCESS FOR THE PREPARATION OF A WATER-SOLUBLE COMPLEX OF 2-(4'-THIAZOLYL)BENZIMIDAZOLE AND FOR THE PREPARATION OF ANTHELMINTIC FUNGICIDAL COMPOSITIONS

DESCRIPTION OF THE INVENTION

The 2-(4'-thiazolyl)benzimidazole (generic name thiabendazole) is widely used as a fungicide (U.S. Pat. No. 3,370,957) and as an anthelmintic (U.S. Pat. No. 3,017,415). A disadvantage of this compound is its very low water-solubility, due to which the compound has to be used in the form of finely divided powders, emulsions, emulsifiable concentrates etc. For certain uses, especially as a fungicide for the protection of citrus fruit against attack by fungi, it is desirable to use the compound in the form of a solution, as the use of dispersions of the solid substance has the effect of decreasing the gloss of the fruits. Also, a solution of the substance is preferred rather than a dispersion of the solid in case of use as an anthelmintic in the drinking water of animals, because there is danger of the dispersion becoming instable on dilution with water which results in undesirable differences in concentration.

Not only thiabendazole-base, but also most of its salts formed with acids have a particularly low water-solubility. Exceptions known up to now are the hypophosphite (U.S. Pat. No. 3,535,331) and the complex formed with lactic acid (U.S. Pat. No. 3,658,827). As appears from U.S. Pat. No. 3,658,827 the hydrochloride, citrate and salicylate show a water-solubility of 0.8, 0.4 and 0.05% (w/v) respectively.

It was found that the complex of thiabendazole with glycolic acid has a solubility in water of about 30% by weight. The concentrated solution is stable, that is to say that no crystallization will occur on storage during long periods of time at room temperature. Further, the concentrated solution may be diluted with water in any desired ratio resulting in stable solutions.

The present complex may be obtained by reacting thiabendazole with glycolic acid in a molar ratio of at least 1:1. The base dissolves readily in a molar excess of up to 10 moles of glycolic acid per mole of thiabendazole. Heating is not necessary, but heating to a temperature lower than 70° increases the rate of dissolution.

As compared with hypophosphorous acid and lactic acid, glycolic acid is considerably less expensive. Surprisingly, the glycolic acid complex shows a water-solubility which is still higher than that of the lactic acid complex, and it has a very much better solubility than thiabendazole complexes with other hydroxycarboxylic acids.

For comparison, the solubility of thiabendazole in 50% by weight solutions of some acids in water was determined. The solubility values found are stated in the following table. The table also shows whether a precipitate was formed on dilution with water to form a 2% (w/v) solution.

| Acid | Solubility % (w/v) | Remarks |
|---|---|---|
| glycolic acid | 29 | clear |
| β-hydroxy valerianic acid | 12.5 | precipitate |
| 2-hydroxy hexanoic acid | 11.8 | precipitate |
| α,β-dihydroxy propionic acid (technical) | 3 | clear |
| gluconic acid (technical) | 2.5 | clear |
| lactic acid | 11.1 | clear |
| propionic acid | 4 | clear |
| acetic acid | 5.5 | clear |

The thiabendazole glycolic acid complex shows the same biological properties as thiabendazole and may be used in all of the cases in which thiabendazole is indicated. Consequently, the invention also relates to a process for the preparation of anthelmintic and fungicidal compositions in which a complex of thiabendazole with glycolic acid is used as the active substance.

In certain cases it is desirable to combine the thiabendazole glycolic acid complex with other pesticidal substances such as fungicides and/or bactericides so as to obtain a composition having a broader activity spectrum. A useful class of additional active substances to be used together with a thiabendazole glycolic acid complex in the compositions of the invention consists of pesticidal nitrogen bases, although any other suitable pesticidal compound may be used. If such nitrogen bases are used as additional active compounds it is highly desirable to use the bases in a form which is soluble in water and compatible with the thiabendazole glycolic acid complex. It was found that glycolic acid complexes of such pesticidal nitrogen bases excellently meet these requirements.

The glycolic acid complexes which may be used together with the glycolic acid complex of thiabendazole in the compositions of the invention may be derived from various classes of pesticidal nitrogen bases. As examples of such nitrogen bases, the following may be mentioned:

1. Fungistatically active quinoline compounds such as 8-hydroxyquinoline and 5-acetyl 8-hydroxyquinoline. Both of these compounds are, in the form of the bases, practically insoluble in water, and the sulphate of 5-acetyl 8-hydroxyquinoline has a water-solubility of not more than 1% by weight. In contrast herewith, the glycolic acid complexes of these compounds may be diluted with water in all proportions.

2. Imidazole derivatives, such as 1[2-(2,4-dichlorophenyl)-2-(2-propenyloxy)ethyl]-1H-imidazole (Imazalil). This fungicide shows a very low solubility in water. Salts with inorganic acids are strongly irritating, although they have a reasonably high water-solubility. The nitrate hydrolyses in water. The glycolic acid complex of this substance may be mixed with water in all proportions and is completely compatible with thiabendazole glycolic acid complexes.

3. Benzimidazole derivatives, such as benzimidazoles containing at position 2 a thiazolyl, thiadiazolyl or isothiazolyl radical. These compounds are known as fungicides (U.S. Pat. No. 3,370,957) and anthelmintics (U.S. Pat. No. 3,017,415). They have a very low water-solubility, and this is also true for the hydrochlorides, citrates and salicylates. Glycolic acid complexes, however, may be mixed with water in all proportions. An important representative of this class of compounds is the 2-(4'-thiazolyl)benzimidazole (thiabendazole), which in the form of its glycolic acid complex, is always present as a constituent of the present compositions.

The systemic fungicide methyl benzimidazolyl-2-carbamate also belongs to this group of benzimidazole compounds.

4. Aliphatic amines having pesticidal activity. As examples of this class may be mentioned 2-aminobutane and 1.5-dicyclohexyl-3-(3-amino 2-hydroxypropylamino) pentane. The 2-aminobutane is a fungicide which is volatile and inflammable. The glycolic acid complex is miscible with water in all proportions and is completely compatible with thiabendazole glycolic acid complexes.

The 1,5-dicyclohexyl-3-(3-amino 2-hydroxypropylamino) pentane is an active bactericide which in the form of the base is a viscous liquid having an ammonia-like odor. The dihydrochloride is a powder which has a strongly irritating effect on the mucous membranes. The base is sparingly soluble in water. The glycolic acid complex is completely miscible with water and, contrary to the dihydrochloride, compatible with the glycolic acid complex of thiabendazole.

The compositions of the present invention are excellently suitable for seed dressing, including the treatment of seed potatoes so as to protect these against attack by fungi and bacteria. Further the compositions may be used successfully for the treatment of fruits after harvesting, especially citrus fruits and bananas, as well as for the treatment of sugar beets after harvesting. A combination of thiabendazole and 8-hydroxyquinoline, both in the form of the glycolic acid complex, may be used successfully in the water of cut flowers thereby prolonging the vase-life of the flowers considerably.

Although the organic nitrogen bases, which together with the glycolic acid complex of thiabendazole, are incorporated in the present compositions may, in some cases, be converted into water soluble salts with strong inorganic acids, for example sulphates or hydrochlorides. These salts cannot be used together with the glycolic acid complex of thiabendazole, because there would be danger for precipitation of a sparingly soluble salt of thiabendazole. Moreover, the salts of these nitrogen bases formed with strong acid often show considerable phytotoxicity.

As stated above, the fungicidal compositions may be used for combatting fungi on a variety of materials and plants as well as for combatting human or animal fungus infections, as is discussed in more detail in U.S. Pat. No. 3,370,957. Also, compositions for use as anthelmintics may be prepared. These compositions may be, for example, pharmaceutical compositions for humans or animals, animal feed or animal feed concentrates. The preparation of such compositions is carried out in a manner known per se.

The following examples illustrate the invention and it will be apparent to those skilled in the art that the examples are illustrative only.

EXAMPLE 1

Thiabendazole (30 g.; technical grade) is mixed with 70 g. of technical grade glycolic acid containing 70% by weight of glycolic acid (inclusive of glycolide), by first preparing a smooth paste with a part of the glycolic acid and mixing the paste with the rest of the glycolic acid. A clear solution of low viscosity having a specific gravity of 1.33 is obtained. Consequently, the concentration of the solution is 30% by weight or 40% (w/v).

On storage at 5° C. the concentrate remains clear for several weeks. On storage at room temperature a small amount of precipitate occurs after some weeks. The concentrate may be diluted with water in any desired ratio.

EXAMPLE 2

Thiabendazole (30 g.; technical grade) is mixed with 0.1 g. nonylphenolpolyglycolether (8 moles of epoxyethane per mole of nonylphenol). The mixture is blended with 73 g. of glycolic acid (70%) and the volume is brought to 100 ml. with distilled water.

This 30% (w/v) concentrate remains stable at room temperature as well as at 0° C. As it possesses a low viscosity, the solution can be atomized as such to protect potatoes against fungal attack. The solution may be diluted with water in any desired ratio.

EXAMPLE 3

To 700 g. of glycolic acid (70%) are added with stirring 2.5 g. of arkopal N-100 (nonylphenol polyglycol ether from 10 moles of ethylene oxide and then, with continuous stirring, 150 g. of thiabendazole and 150 g. of 8-hydroxyquinoline. Finally, 2.5 g. of polyvinylpyrrolidone are added and the volume is brought to 1000 ml. with deionized water (about 227 g.)

The liquid so obtained is miscible with water in all proportions, and may be used as such as a seed dressing, especially for the treatment of seed potatoes for combatting fungi. The composition is very effective against Rhizoctonia and is, as far as this activity is concerned, comparable with organic mercury compounds.

A further important use is in the preservation of cut flowers for prolonging the vase-life.

EXAMPLE 4

The following composition is prepared in the way indicated in Example 3:

| | |
|---|---|
| Thiabendazole | 150 g. |
| 5-acetyl 8-hydroxyquinoline | 150 g. |
| Glycolic acid (70%) | 680 g. |
| Arkopal N-100 | 2.5 g. |
| Polyvinylpyrrolidone | 2.5 g. |
| Water | to 1000 ml. |

This composition is miscible with water in all proportions and has the same utilities as the compositions prepared according to Example 3.

EXAMPLE 5

The following composition is prepared in the way described in Example 3:

| | |
|---|---|
| Thiabendazole | 100 g. |
| Imazalil-base | 25 g. |
| Glycolic acid | 740 g. |
| Arkopal N-080 | 2 g. |
| Keltrol solution (0.5% in water) | 80 g. |
| n-butanol | 100 g. |
| Water | to 1000 ml. |

This composition may be used as such as a seed dressing for cereal grains, in particular for barley. The main diseases of barley, e.g. helmintosporium, are controlled by this composition more effectively than with organomercurials. The treatment does not show phytotoxic effects.

EXAMPLE 6

Nonylphenolpolyglycolether (1 g.) is added to 788 g. glycolic acid (70%), and 40 g. of thiabendazole is dissolved in this mixture with stirring. The mixture is then cooled to about 10° C. and 200 g. of 2-aminobutane is added, thereby taking care that the temperature does not rise above 35° C. Finally, the volume is brought to 1 liter with water.

The composition is miscible with water in all proportions, has an agreeable odor and is as such useful for combatting fungi, for example for treating seed potatoes against phoma diseases.

EXAMPLE 7

To 500 g. of glycolic acid (70%) is added 100 g. of 1,5-dicyclohexyl 3-(3-amino 2-hydroxypropylamino) pentane and the mixture is stirred until a solution is obtained. Then 250 g. of thiabendazole and 350 g. of glycolic acid (70%) are added, and the volume is brought to 1 liter with water (about 50 ml.).

What is claimed is:

1. A water soluble complex of 2-(4'-thiazolyl) benzimidazole with glycolic acid.

2. Anthelmintic and fungicidal composition containing an anthelmintically or fungicidally effective amount of a water-soluble complex of 2-(4'-thiazolyl) benzimidazole with glycolic acid, optionally containing one or more glycolic acid complexes of a pesticidal nitrogen base.

3. Composition according to claim 2 wherein the additional active compound is a glycolic acid complex of 8-hydroxyquinoline.

4. Composition according to claim 2 wherein the additional active compound is a glycolic acid complex of 5-acetyl-8-hydroxyquinoline.

5. Composition according to claim 2 wherein the additional active compound is a glycolic acid complex of 1-[2-(2,4-dichlorophenyl)-2-(2-propenyloxy)ethyl]-1H-imidazole.

6. Composition according to claim 2 wherein the additional active compound is a glycolic acid complex of 1,5-dicyclohexyl-3-(3-amino-2-hydroxypropylamino)pentane.

7. Composition according to claim 2 wherein the additional active compound is a glycolic acid complex of 2-aminobutane.

* * * * *